United States Patent
Peterson

(10) Patent No.: US 9,492,664 B2
(45) Date of Patent: Nov. 15, 2016

(54) SYSTEM AND METHOD FOR PERFORMING PERCUTANEOUS NERVE FIELD STIMULATION WITH CONCURRENT ANODE INTENSIFIED SPINAL CORD STIMULATION

(75) Inventor: David K. L. Peterson, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1541 days.

(21) Appl. No.: 12/820,971

(22) Filed: Jun. 22, 2010

(65) Prior Publication Data
US 2010/0331925 A1 Dec. 30, 2010

Related U.S. Application Data

(60) Provisional application No. 61/220,146, filed on Jun. 24, 2009.

(51) Int. Cl.
*A61N 1/34* (2006.01)
*A61N 1/36* (2006.01)
*A61N 1/05* (2006.01)

(52) U.S. Cl.
CPC ......... *A61N 1/36071* (2013.01); *A61N 1/0551* (2013.01)

(58) Field of Classification Search
USPC ................. 607/46, 48, 49, 115–117
See application file for complete search history.

(56) References Cited

U.S. PATENT DOCUMENTS

| | | | |
|---|---|---|---|
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,539,538 B2 | 5/2009 | Parramon et al. | |
| 7,650,184 B2 | 1/2010 | Walter | |
| 2003/0139781 A1 | 7/2003 | Bradley et al. | |
| 2005/0267546 A1 | 12/2005 | Parramon et al. | |
| 2007/0142863 A1 | 6/2007 | Bradley | |
| 2007/0150034 A1* | 6/2007 | Rooney et al. | 607/115 |
| 2007/0150036 A1 | 6/2007 | Anderson | |
| 2007/0168004 A1 | 7/2007 | Walter | |
| 2007/0168007 A1 | 7/2007 | Kuzma et al. | |
| 2007/0276450 A1* | 11/2007 | Meadows et al. | 607/46 |

(Continued)

OTHER PUBLICATIONS

Paicius, Richard, et al., "Peripheral Nerve Field Stimulation for the Treatment of Chronic Low Back Pain: Preliminary Results of Long-Term Follow-Up: A Case Series," Neuromodulation Technology at the Neural Interface, vol. 10, No. 3 (2007) (12 pages).

(Continued)

*Primary Examiner* — Allen Porter, Jr.
(74) *Attorney, Agent, or Firm* — Schwegman Lundberg & Woessner, P.A.

(57) ABSTRACT

A method of providing therapy to a patient comprising sinking first electrical current into at least a first one of a plurality of electrodes adjacent the spinal cord tissue, thereby providing therapy to a first region of the patient. The method further comprises sinking second electrical current into at least one electrode adjacent peripheral tissue remote from the spinal cord tissue, thereby providing therapy to a second region of the patient. The method further comprises sourcing at least a portion of the first electrical current and at least a portion of the second electrical current into at least a second one of the plurality of electrodes.

20 Claims, 12 Drawing Sheets

(56) References Cited

U.S. PATENT DOCUMENTS

2009/0024189 A1    1/2009  Lee et al.

OTHER PUBLICATIONS

Krutsch, Jason P. et al., "A Case Report of Subcutaneous Peripheral Nerve Stimulation for the Treatment of Axial Back Pain Associated with Postlaminectomy Syndrome," Neuromodulation Technology at the Neural Interface, vol. 11, No. 2 (2008) (4 pages).

Bernstein, Clifford, et al.,"Spinal Cord Stimulation in Conjunction with Peripheral Nerve Field Stimulation for the Treatment of Low Back and Leg Pain: A Case Series," Neuromodulation Technology at the Neural Interface, vol. 11, No. 2 (2008) (8 pages).

\* cited by examiner

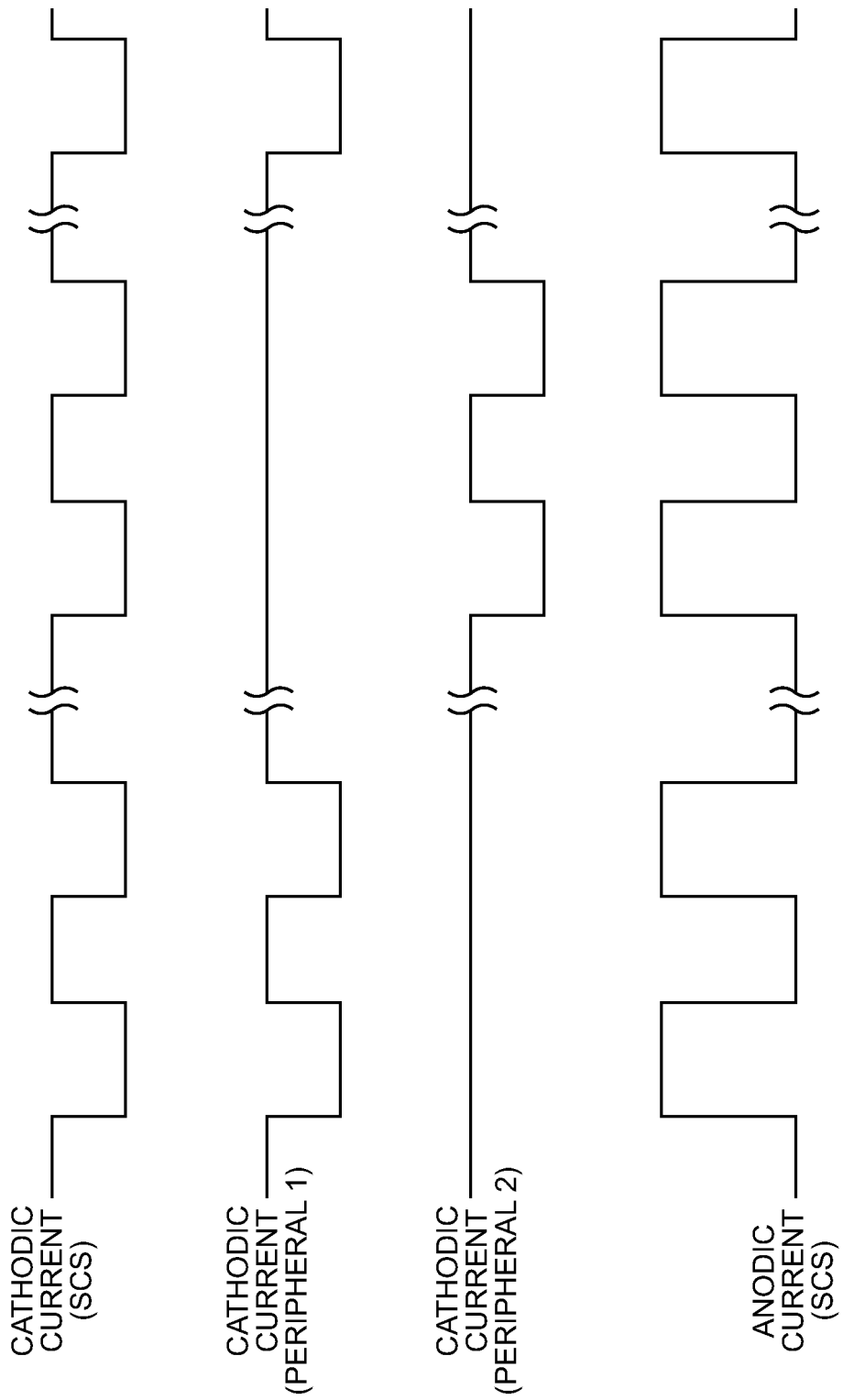

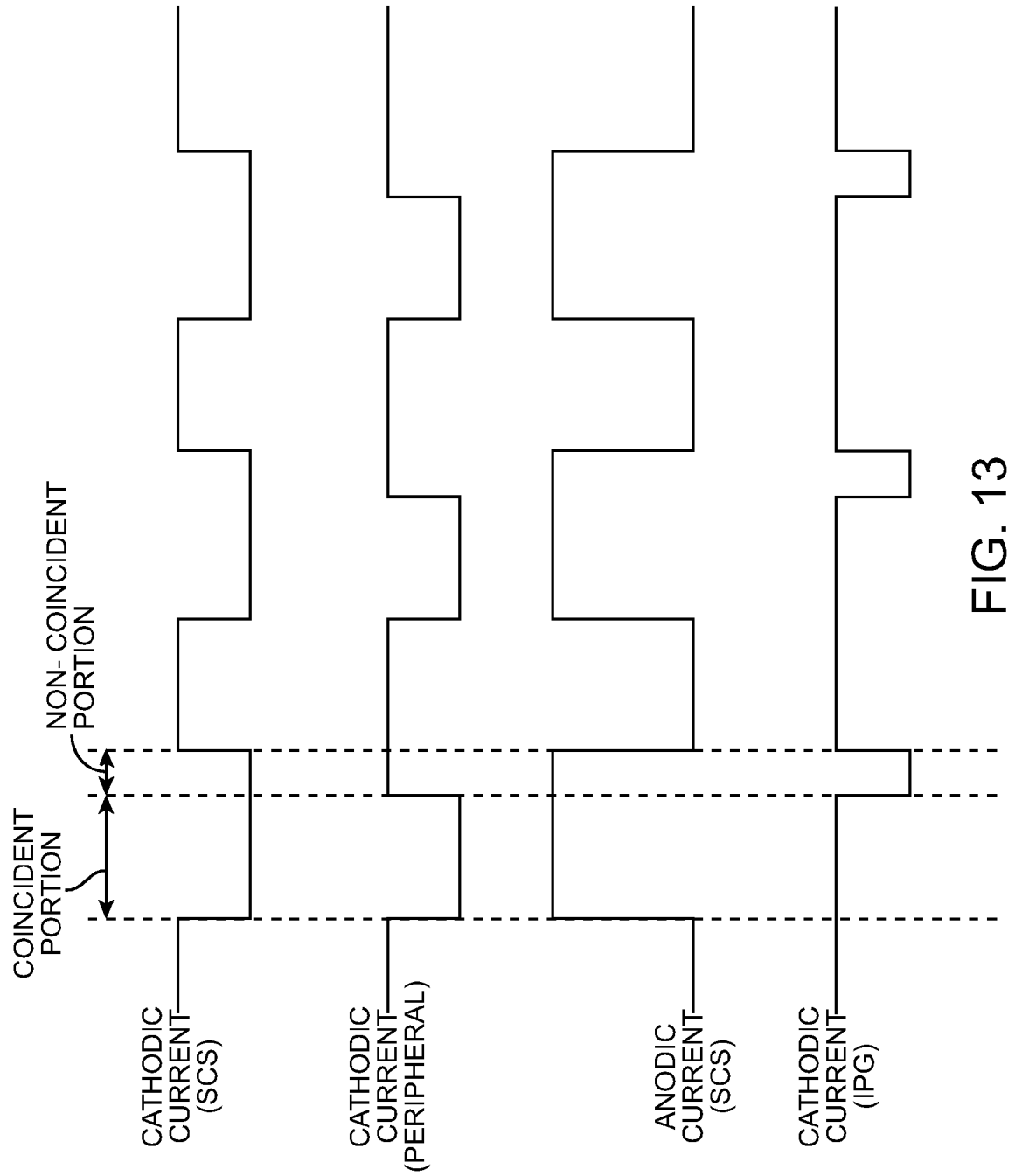

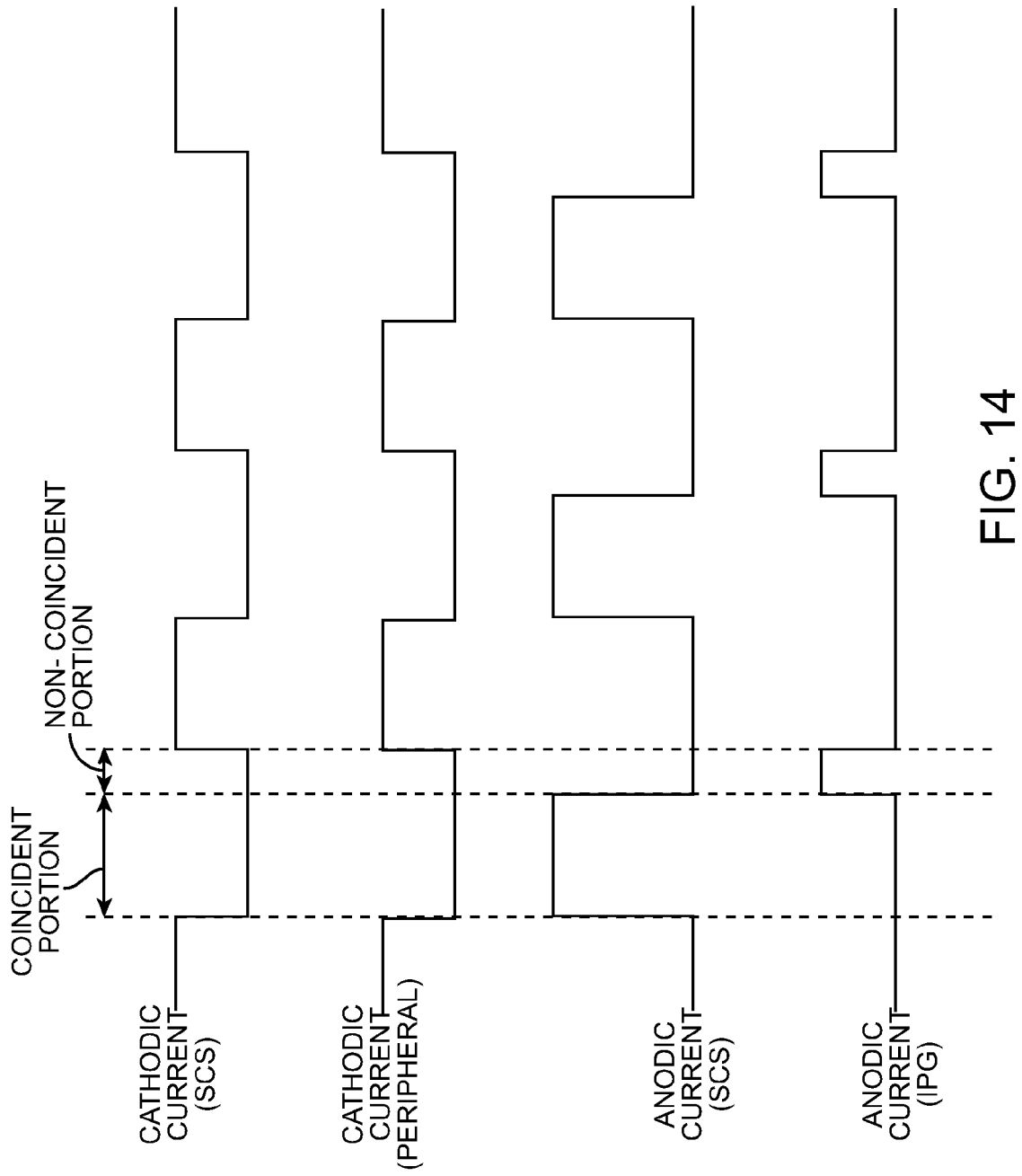

SYSTEM AND METHOD FOR PERFORMING PERCUTANEOUS NERVE FIELD STIMULATION WITH CONCURRENT ANODE INTENSIFIED SPINAL CORD STIMULATION

RELATED APPLICATION

The present application claims the benefit under 35 U.S.C. §119 to U.S. provisional patent application Ser. No. 61/220,146, filed Jun. 24, 2009. The foregoing application is hereby incorporated by reference into the present application in its entirety.

FIELD OF THE INVENTION

The present invention relates to tissue stimulation systems, and more particularly, to a system and method for conditioning and stimulating nerve fibers.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic pain syndromes, and the application of spinal cord stimulation has begun to expand to additional applications, such as angina pectoralis and incontinence. In recent investigations, Peripheral Stimulation (PS), which includes Peripheral Nerve Field Stimulation (PNFS) techniques that stimulate nerve tissue directly at the symptomatic site of the disease or disorder (e.g., at the source of pain), and Peripheral Nerve Stimulation (PNS) techniques that directly stimulate bundles of peripheral nerves that may not necessarily be at the symptomatic site of the disease or disorder, has demonstrated efficacy in the treatment of chronic pain syndromes and incontinence, and a number of additional applications are currently under investigation.

SCS has become an accepted therapeutic modality for the treatment of a wide variety of clinical pain syndromes. However, despite many reports of success in relieving radicular pain in the lower extremities and buttocks with SCS, physicians often report difficulties with achieving and maintaining adequate pain control over the long term for patients experiencing axial low back pain, especially for patients experiencing chronic pain due to failed back surgery syndrome (FBSS). Thus, SCS is often inadequate in relieving both the back and leg pain components. However, for patients with chronic low back pain as a result of FBSS, it has been shown that PNFS is extremely effective in reducing pain and enabling patients to resume their normal activities (see Richard M. Paicius, M.D., et al., *Peripheral Nerve Field Stimulation for the Treatment of Chronic Low Back Pain: Preliminary Results of Long-Term Follow-up: A Case Series*, Neuromodulation Technology at the Neural Interface, Volume 10, Number 3, 2007, and Jason P. Krutsch, M.D., et al., *A Case Report of Subcutaneous Peripheral Nerve Stimulation for the Treatment of Axial Back Pain Associated with Postlaminectomy Syndrome*," Neuromodulation Technology at the Neural Interface, Volume 11, Number 2, 2008).

Thus, the use of PNFS as an adjunct to SCS may overcome the limitations of SCS, and may be valid option for the treatment of patients whose pain is severe both in the axial back and legs, with the SCS component targeting the radicular pain, and the PNFS more directly and completely relieving the lower back pain. Based on case studies performed on patients, it has been found that a combination of SCS and PNFS to control lower back and leg pain is, indeed, more effective than either modality alone. Thus, it can be concluded that PNFS may be used in combination with SCS as a safe and effective alternative treatment for patients with chronic low back and leg pain (see Clifford A. Bernstein, M.D., et al., *Spinal Cord Stimulation in Conjunction with Peripheral Nerve Field Stimulation for the Treatment of Low Back and Leg Pain: A Case Series*, Neuromodulation Technology at the Neural Interface, Volume 11, Number 2, 2008).

An implantable neurostimulation system, whether used in the context of SCS or PNFS, typically includes one or more electrode carrying stimulation leads, which are implanted at the desired stimulation site. In SCS, the stimulation lead(s) are implanted within the epidural space of the patient to stimulate the spinal cord tissue, whereas in PNFS, the stimulation lead(s) are implanted in the subcutaneous tissues of a peripheral region, such as the lower back region, to directly stimulate the peripheral field (i.e., the region of the affected nerves, the cutaneous afferents, or the dermatomal distribution of these nerves, which then converge back on the spinal cord) in the region of pain.

The implantable neurostimulation system further includes a neurostimulator (e.g., an implantable pulse generator (IPG)) implanted within a tissue pocket remotely from the stimulation site, but coupled to the stimulation lead(s). Thus, electrical pulses can be delivered from the neurostimulator to the stimulation lead(s) to stimulate or activate a volume of neural tissue. In particular, electrical energy conveyed between at least one cathodic electrode and at least one anodic electrodes creates an electrical field, which when strong enough, depolarizes (or "stimulates") the neurons beyond a threshold level, thereby inducing the firing of action potentials (APs) that propagate along the neural fibers.

Stimulation energy may be delivered to the electrodes during and after the lead placement process in order to verify that the electrodes are stimulating the target neural elements and to formulate the most effective stimulation regimen. The regimen will dictate which of the electrodes are sourcing current pulses (anodes) and which of the electrodes are sinking current pulses (cathodes) at any given time, as well as the magnitude, duration, and rate of the current pulses. The stimulation regimen will typically be one that provides stimulation energy to all of the target tissue that must be stimulated in order to provide the therapeutic benefit, yet minimizes the volume of non-target tissue that is stimulated. In the case of SCS, such a therapeutic benefit is accompanied by "paresthesia," i.e., a tingling sensation that is effected by the electrical stimuli applied through the electrodes.

While the electrical stimulation of neurons has generally been successful in providing a therapeutic benefit to the patient, there are instances where the target tissue is not directly adjacent to an electrode and, because the electrical field strength decreases exponentially with distance from the electrodes, a relatively strong electrical field must be created to generate APs in the target neural fibers. The electrical field may, however, also result in the generation of APs in the non-target neural fibers between the electrode and the target neural fibers. The generation of APs in the non-target neural fibers may, in turn, lead to undesirable outcomes (e.g., discomfort or involuntary movements) for the patient. Because the target neural tissue (i.e., the tissue associated with the therapeutic effects) and non-target neural tissue (i.e., the tissue associated with undesirable side effects) are often juxtaposed, therapeutically stimulating neural tissue while preventing side effects may be difficult to achieve. In the context of SCS, there may be a few ways of eliminating, or at least minimizing, the stimulation of non-target neural tissue.

For example, in the case of SCS, where the electrode array is medio-laterally aligned (i.e., the electrodes are arranged transversely to the neural fibers of the spinal cord), it may be desirable to control the shape of the AP generating neural region of the spinal cord in order to prevent the generation of APs in non-target neural fibers. For example, to produce the feeling of paresthesia without inducing involuntary motor movements within the patient, it is often desirable to preferentially stimulate nerve fibers in the dorsal column (DC) nerve fibers, which primarily include sensory nerve fibers, over nerve fibers in the dorsal roots (DR) nerve fibers, which include both sensory nerve fibers and motor reflex nerve fibers.

While DC nerve fibers are the intended targets in conventional SCS, in fact, the DR nerve fibers often are recruited first because of geometric, anatomical, and physiological reasons. For example, the DR nerve fibers have larger diameters than the largest nearby DC nerve fibers, and thus, have a lower threshold at which they are excited. Other factors that contribute to the lower threshold needed to excite DR nerve fibers are the different orientations of the DC nerve fibers and DR nerve fibers, the curved shape of the DR nerve fibers, and the inhomogeneity and anisotropy of the surrounding medium at the entrance of the DR nerve fibers into the spinal cord. Thus, DR nerve fibers may still generate APs at lower voltages than will nearby DC nerve fibers. As a result, the DC nerve fibers that are desired to be stimulated have a lower probability to be stimulated than do the DR nerve fibers, and thus, the reflex motor nerve fibers intermingled among the sensor nerve fibers of a dorsal root are often recruited, leading to discomfort or muscle twitching, thereby preventing satisfactory paresthesia coverage.

For reasons such as these, it is often desirable to modify the threshold at which neural tissue is activated in a manner that maximizes excitation of the target neural tissue, while minimizing excitation of the non-target neural tissue; for example by increasing the DR/DC threshold ratio. This can be accomplished by sinking an electrical pulse to a cathodic electrode located at the center of the spinal cord to depolarize the target tissue adjacent the cathodic electrode, thereby creating APs along the DC nerve fibers, while an electrical pulse can be sourced to anodic electrodes on both sides of the cathodic electrode to hyperpolarize non-target tissue adjacent the anodic electrodes, thereby increasing the threshold of the DR nerve fibers.

As another example, in the case where the electrode array is rostro-caudally aligned (i.e., the electrodes are arranged along the neural fibers of the spinal cord), it may be desirable to induce APs in a bundle of target nerve fibers, and to the extent that APs are induced in bundle of non-target nerve fibers, block APs within the non-target nerve fibers from reaching the brain or any other parts of the nervous system. In particular, an electrical pulse can be sunk to a cathodic electrode to depolarize target tissue adjacent the cathodic electrode, thereby creating APs along a first bundle of nerve fibers, while an electrical pulse can be sourced to one or more anodic electrodes above or below the cathodic electrode to hyperpolarize non-target tissue adjacent the anodic electrode(s), thereby blocking any APs along a second bundle of nerve fibers that were inadvertently induced by the sink electrical pulse of the cathodic electrode.

Because the amount of electrical current that is sourced must equal the amount of electrical current that is sunk, the amount of sourced electrical current must be limited in order to minimize the adverse effects that could potentially occur as a result of the increased amount of the sunk electrical current. For example, in the previously described case where the electrode array is medio-laterally aligned, an increase in the electrical current sunk by the cathode as a result of an increase in the electrical current sourced by the anodes may result in the generation of APs in non-target DC nerve fibers. In the previously described case where the electrode array is rostro-caudally aligned, an increase in the electrical current sunk by the cathode as a result of an increase in the electrical current sourced by the anodes(s) may result in the generation of APs in non-target nerve fibers that are not blocked by the sourced electrical current.

To limit the amount of current sunk by a cathode, it is known to redistribute some of the cathodic current to a large surface area, such as the case of the IPG. Such a technique is described in U.S. Patent Application Publication No. 2007/0142863, entitled "Apparatus and Methods for Stimulating Tissue," which is expressly incorporated herein by reference. By distributing the cathodic current to a surface area that has no, or very little, effect on the neural tissue, the magnitude of the electrical pulses sourced by the anodes can be increased, while avoiding a commensurate increase in the magnitude of the electrical pulses sunk to the cathode that is adjacent the neural tissue. In this manner, any adverse effects that may otherwise occur as a result of an increase in the electrical current sunk to the cathodic electrode, and thus conveyed through the neural tissue adjacent the cathodic electrode, can be minimized.

While this electrical current redistribution technique is beneficial, inadvertent stimulation of tissue in the pocket in which the neurostimulator is implanted may occur. This pocket stimulation problem is exacerbated when a microstimulator, which is an implantable neurostimulator in which the body or case of the device is compact (typically on the order of a few millimeters is diameter by several millimeters to a few centimeters in length), is used to convey energy to the stimulation lead. Because the case of a microstimulator is relatively small, the current density on the surface of the case may be quite high when the microstimulator is operated in a monopolar mode. As a result, undesired and perhaps annoying or painful stimulation in the implantation pocket might be expected.

There, thus, remains a need for an alternative neurostimulation method and system that minimizes any adverse effects that may result in an increase in cathodic current when the anodic current is increased.

SUMMARY OF THE INVENTION

In accordance with the present inventions, a method of providing therapy to a patient is provided. The method comprises concurrently sinking first electrical current into at least a first electrode adjacent the spinal cord tissue, and second electrical current into at least one electrode adjacent peripheral tissue (e.g., the lower back) remote from the spinal cord tissue. One method may further comprise implanting the electrodes adjacent the spinal cord tissue and peripheral tissue. The sinking of the first electrical current provides therapy to a first region of the patient (e.g., a leg region), and the sinking of the second electrical current provides therapy to a second region of the patient (e.g., a lower back region). The method further comprises sourcing at least a portion of the first electrical current and at least a portion of the second electrical current into at least a second electrode adjacent the spinal cord tissue. In one method, all of the first and second electrical currents is sourced into the second electrode(s) adjacent the spinal cord tissue.

In one method, each of the first and second electrical currents comprises a plurality of electrical pulses. The electrical pulses of the first and second electrical currents may be concurrent. Or, the first and second electrical current may have different pulse widths.

As one example, the pulse width of the first electrical current may be longer than the pulse width of the second electrical current, such that the pulse width of the first electrical current has a portion that is temporally coincident with the pulse width of the second electrical current, and a portion that is not temporarily coincident with the pulse width of the second electrical current. In this case, the second electrical current (or a portion thereof) is sunk into the electrode(s) adjacent the peripheral tissue during the coincident portion of the pulse width, and the second electrical current (or a portion thereof) is sunk into either or both of a case of an implantable pulse generator and at least one other electrode adjacent the peripheral tissue during the non-coincident portion of the pulse width.

As another example, the pulse width of the first electrical current may be shorter than the pulse width of the second electrical current, such that the pulse width of the second electrical current has a portion that is temporally coincident with the pulse width of the first electrical current, and a portion that is not temporarily coincident with the pulse width of the first electrical current. In this case, the second electrical current (or a portion thereof) is sourced into the second electrode(s) adjacent the spinal cord tissue during the coincident portion of the pulse width, and is sourced into any combination of a case of an implantable pulse generator, at least one other electrode adjacent the peripheral tissue, and at least a third electrode adjacent the spinal cord tissue during the non-coincident portion of the pulse width.

In an optional method, the second electrical current is cycled on and off while continually sinking the first electrical current. In this case, the second electrical current may be sunk into a case of an implantable pulse generator when the second electrical current is cycled off at the electrode(s) adjacent the peripheral tissue. Or, the second electrical current may be sunk into at least another electrode adjacent the peripheral tissue, thereby providing therapy to a third region of the patient, with the sinking of the second electrical current into the other electrode(s) adjacent the peripheral tissue being cycled on when the second electrical current sunk into the first electrode(s) adjacent the peripheral tissue is cycled off.

In one method, electrodes are arranged medio-laterally along the spinal cord tissue. In this case, the first electrode(s) can be adjacent to dorsal column neural fibers of the spinal cord tissue, the second electrode(s) can be adjacent to dorsal root neural fibers of the spinal cord tissue, the sunk cathodic electrical current can generate action potentials in the dorsal column neural fibers of the spinal cord tissue, and the sourced anodic electrical current can increase the action potential threshold of the dorsal root neural fibers. In another exemplary method, the electrodes are arranged rostro-caudally along the spinal cord tissue. In this case, the first electrode(s) can be a first distance from the first neural fiber bundle and a second greater distance from the second neural fiber bundle, the sunk cathodic electrical current can generate action potentials in the first and second neural fibers bundles, and the sourced anodic electrical current can block at least some of the action potentials in the first neural fiber bundle.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 12 is a graph of pulse timing diagrams used to sink and source electrical current pulses in accordance with another technique of the present inventions;

FIG. 13 is a graph of pulse timing diagrams used to sink and source electrical current pulses in accordance with still another technique of the present inventions; and FIG. 14 is a graph of pulse timing diagrams used to sink and source electrical current pulses in accordance with yet another technique of the present inventions.

DETAILED DESCRIPTION OF THE EMBODIMENTS

Figure 1:
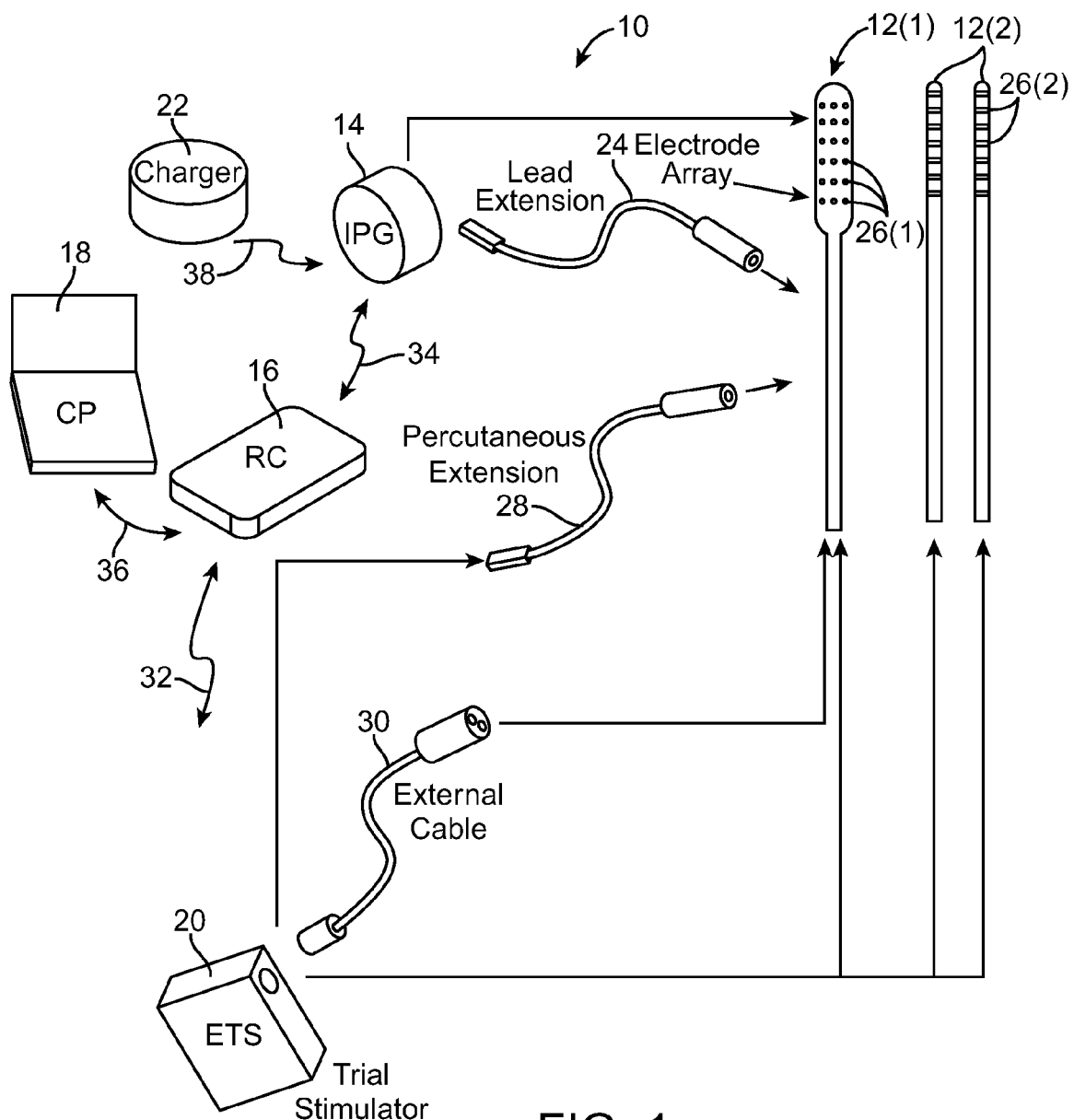
FIG. 1 is plan view of one embodiment of a nerve tissue stimulation system arranged in accordance with the present inventions.

Turning first to FIG. 1, an exemplary nerve tissue stimulation system 10 is used to perform both Spinal Cord Stimulation (SCS) and Peripheral Nerve Field Stimulation (PNFS) in a manner that uses redistributes any cathodic electrical current in excess of that needed to perform the SCS function to the PNFS function. In doing this, any adverse effect that may occur when the magnitude of the anodic electrical current is increased may be prevented or, at least, minimized. The system 10 generally includes a plurality of implantable stimulation leads 12 (at least one for the SCS function and at least one other one for the PNFS function), a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, a surgical paddle lead 12(1) with a plurality of electrodes 26(1) and two percutaneous leads 12(2) with a plurality of electrodes 26(2) are provided. Although three stimulation leads 12 are illustrated, it should be appreciated that less or more stimulation leads 12 can be provided. For example, two percutaneous stimulation leads 12(1) can be used for the SCS function and an additional two stimulation leads 12 (whether percutaneous leads or surgical paddle leads) can be used for the PNFS function. Or, a single stimulation lead 12 (whether a percutaneous lead or a surgical paddle lead) can be used for the SCS function and a single stimulation lead 12 (whether a percutaneous lead or a surgical paddle lead) can be used for the PNFS function. Optionally, the lead extension 24 can be provided with a splitter (not shown), so that a single lead extension can be used to couple the multiple stimulation leads 12 to a single port on the IPG 14. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
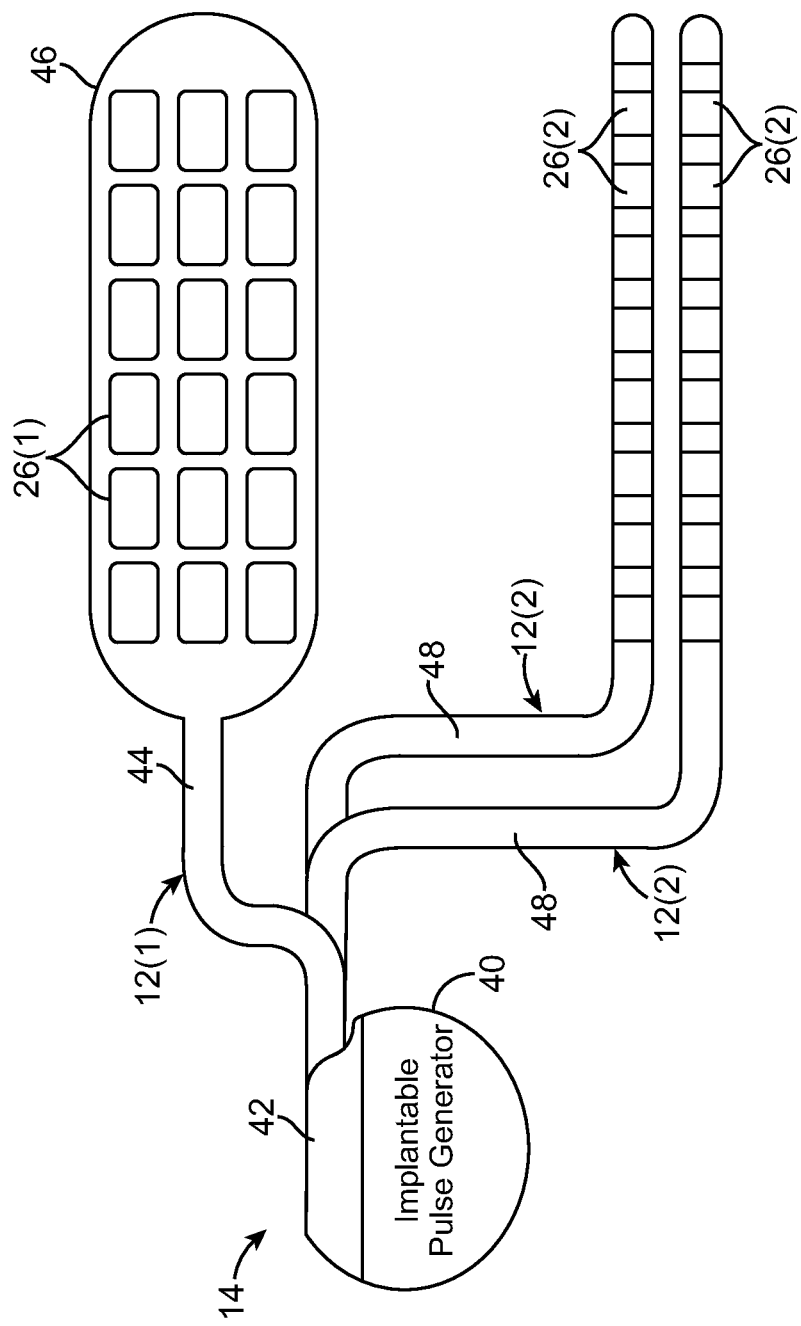
FIG. 2 is a plan view of an implantable pulse generator (IPG) and stimulation leads used in the nerve tissue stimulation system of FIG. 1.

Referring further to FIG. 2, the IPG 14 comprises an outer case 40 for housing the electronic and other components (described in further detail below), and a connector 42 to which the proximal ends of the stimulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As shown in FIG. 2, the surgical paddle lead 12(1) includes an elongated cylindrical lead body 44 and a distally-located paddle 46 with one side on which the electrodes 26(1) are carried. The electrodes 26(1) are arranged in a two-dimensional array in three columns along the axis of the stimulation lead 12(1). In the illustrated embodiment, six rows of electrodes 26(1) are provided, although any number of rows of electrodes can be used. Each row of the electrodes 26(1) is arranged in a line transversely to the axis of the lead 12(1). The actual number of leads and electrodes will, of course, vary according to the intended application. Further details regarding the construction and method of manufacture of surgical paddle leads are disclosed in U.S. Patent Application Publication No. 2007/0150036, entitled "Stimulator Leads and Methods for Lead Fabrication," the disclosure of which is expressly incorporated herein by reference.

Each of the percutaneous stimulation leads 12(2) comprises an elongated cylindrical lead body 48, and the electrodes 26(2) take the form of ring electrodes mounted around the lead body 48. Each of the stimulation leads 12(2) has eight electrodes 26(2). The actual number and shape of leads and electrodes will, of course, vary according to the intended application. Further details describing the construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are expressly incorporated herein by reference.

As will be described in further detail below, the IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 3:
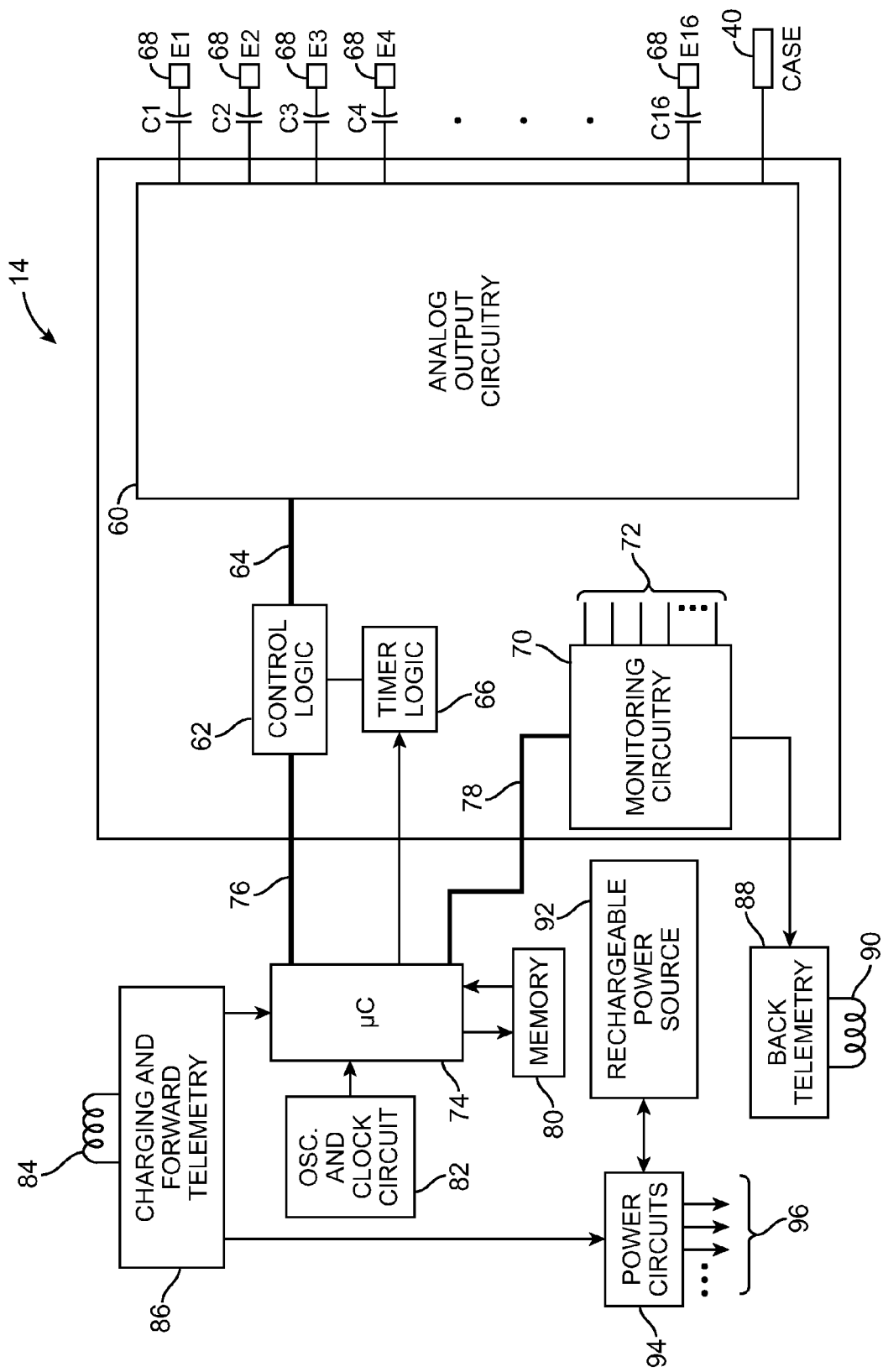
FIG. 3 is a block diagram of the internal components of the IPG of FIG. 1.

Turning next to FIG. 3, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 μs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference. The analog output circuitry 60 may also comprise pulse shaping circuitry (not shown) capable of shaping the pulses (e.g., a square pulse, an exponential pulse, a logarithmic pulse, a ramped pulse, a trapezoidal pulse, etc.). Further details discussing pulse shaping circuitry and the different pulse shapes that can be generated are disclosed in U.S. Pat. No. 8,036,754, entitled "Use of Stimulation Pulse Shape to Control Neural Recruitment Order and Clinical Effect," which is expressly incorporated herein by reference.

The IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical parameter data (e.g., electrode impedance and/or electrode field potential). The IPG 14 further comprises processing circuitry in the form of a microcontroller (μC) 74 that controls the control logic 62 over data bus 76, and obtains status data from the monitoring circuitry 70 via data bus 78. The IPG 14 further comprises memory 80 and oscillator and clock circuit 82 coupled to the μC 74. The μC 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the μC 74 generates the necessary control and status signals, which allow the μC 74 to control the operation of the IPG 14 in accordance with a selected operating program and stimulation parameters. In controlling the operation of the IPG 14, the μC 74 is able to individually generate stimulus pulses at the electrical terminals 68 using the analog output circuitry 60, in combination with the control logic 62 and timer logic circuitry 66, thereby allowing each electrical terminal 68 to be paired or grouped with other electrical terminals 68, including the monopolar case electrode, to control the polarity, amplitude, rate, pulse width, pulse shape, burst rate, and channel through which the current stimulus pulses are provided. The μC 74 facilitates the storage of electrical parameter data measured by the monitoring circuitry 70 within memory 80.

The IPG 14 further comprises a receiving coil 84 for receiving programming data (e.g., the operating program and/or stimulation parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the IPG 14.

The IPG 14 further comprises back telemetry circuitry 88 and a transmission coil 90 for sending informational data to the external programmer. The back telemetry features of the IPG 14 also allow its status to be checked. For example, when the CP 18 initiates a programming session with the IPG 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 92 and power circuits 94 for providing the operating power to the IPG 14. The rechargeable power source 92 may, e.g., comprise a lithium-ion or lithium-ion polymer battery or other form of rechargeable power. The rechargeable source 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits) received by the receiving coil 84.

To recharge the power source 92, the external charger 22 (shown in FIG. 1), which generates the AC magnetic field, is placed against, or otherwise adjacent, to the patient's skin over the implanted IPG 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bi-directional telemetry.

Additional details concerning the above-described and other IPGs may be found in U.S. Pat. No. 6,516,227, U.S. Patent Publication No. 2003/0139781, and U.S. Pat. No. 7,539,538, entitled "Low Power Loss Current Digital-to-Analog Converter Used in an Implantable Pulse Generator," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
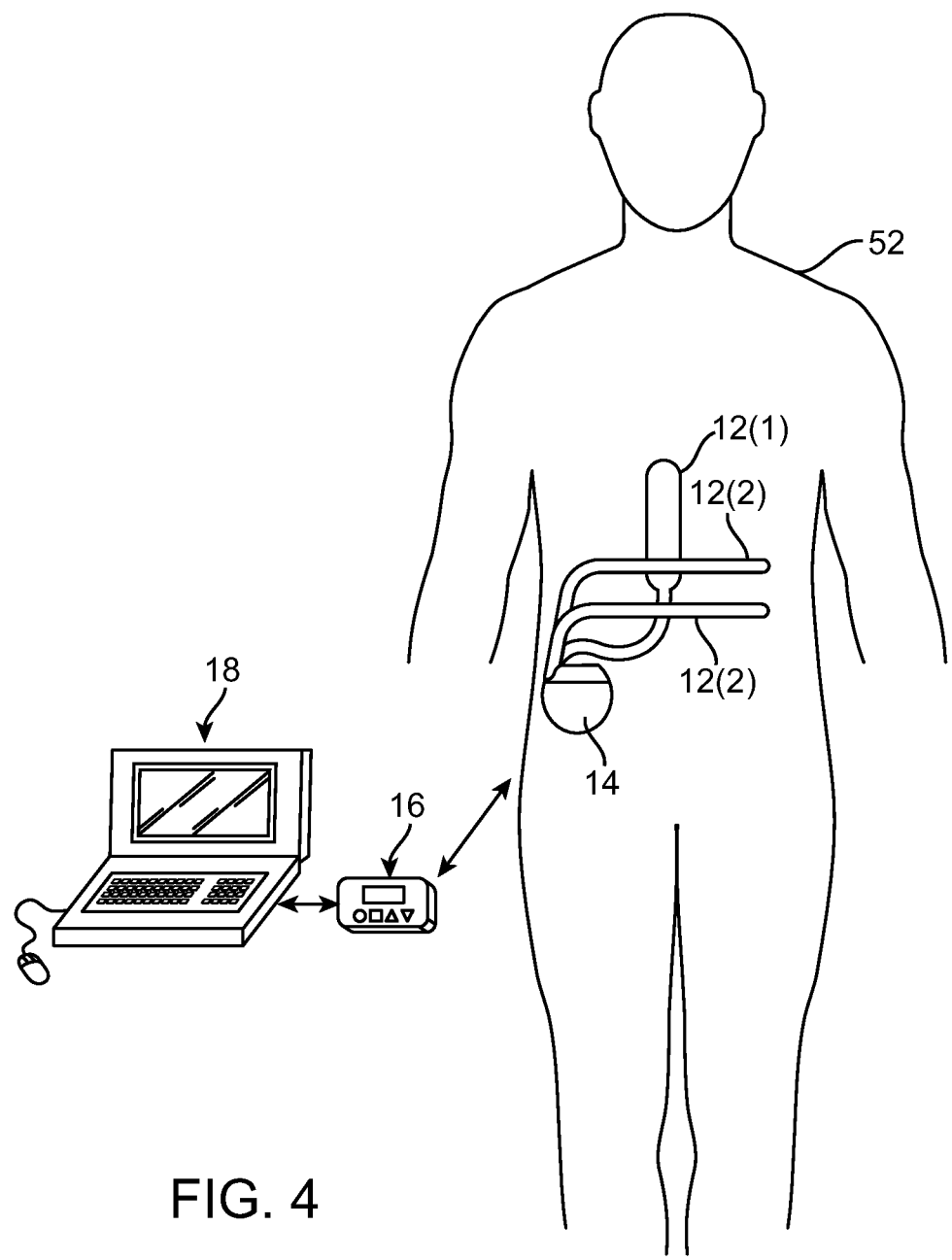
FIG. 4 is a plan view of the nerve tissue stimulation system of FIG. 1 in use with a patient.

For spinal cord stimulation (SCS) applications, the surgical paddle lead 12(1) is implanted within the spinal column of a patient 52, as shown in FIG. 4. The preferred placement of the lead 12(1) is adjacent to the spinal cord area to be stimulated. The surgical paddle lead 12(1) is implanted within the spinal column using a surgical procedure, and specifically, a laminectomy, which involves removal of the laminar vertebral tissue to allow both access to the dura layer and positioning of the lead 12(1).

Alternatively, if percutaneous stimulation leads 12(2) are used, one or more can be introduced, with the aid of fluoroscopy, into the epidural space through a Touhy-like needle, which passes through the skin, between the desired vertebrae, and into the epidural space above the dura layer. For unilateral pain, one stimulation lead 12(2) is placed on the corresponding lateral side of the spinal cord. For bilateral pain, one stimulation lead 12(2) is placed down the midline of the spinal cord, or two stimulation leads 12(2) are placed down the respective sides of the midline. In many cases, a stylet, such as a metallic wire, is inserted into a lumen running through the center of each of the stimulation leads 12(2) to aid in insertion of the lead through the needle and into the epidural space. The stylet gives the lead rigidity during positioning, and once the stimulation lead 12(2) is positioned, the stylet can be removed after which the lead becomes flaccid.

For Peripheral Nerve Field Stimulation (PNFS) applications, the percutaneous stimulation leads 12(2) are implanted remotely from the spinal cord; for example, in the in the subcutaneous tissues of the lower back, directly in the region of maximum pain. As illustrated, the stimulation leads 12(2) are placed laterally (horizontally) across the back of the patient; for example, on both sides of the L4-L5 levels overlying the paraspinous muscles. For the purposes of this specification, peripheral nerve tissue is any nerve tissue that is not part of the central nervous system (i.e., nerve tissue other than the brain or spinal cord). In the illustrated embodiment, the stimulation leads 12(2) are implanted within the lower back of the patient. Alternatively, the stimulation leads 12(2) may be implanted in other region of the patient where peripheral nerves can be stimulated, including the head and cervical regions, abdomen, and limbs. The stimulation leads 12(2) may be implanted in the selected peripheral region using a Touhy-like needle that can be tunneled just under the dermis, with the proper positioning of the stimulation leads 12(2) being confirmed via fluoroscopy.

After proper placement of the stimulation leads 12 at the target areas of the spinal cord and peripheral regions, the leads 12 are anchored in place to prevent movement of the stimulation leads 12. To facilitate the location of the IPG 14 away from the exit point of the stimulation leads 12 implanted within the spinal column, the lead extensions 24 may be used. Whether lead extensions are used or not, the proximal ends of the stimulation leads 12 exiting the spinal column and the stimulation leads 12 implanted within the lower back region are passed through one or more tunnels (not shown) subcutaneously formed along the torso of the patient to a subcutaneous pocket (typically made in the patient's abdominal or buttock area) where the IPG 14 is implanted. The IPG 14 may, of course, also be implanted in other locations of the patient's body. A subcutaneous tunnel can be formed using a tunneling tool over which a tunneling straw may be threaded. The tunneling tool can be removed, the stimulation leads 12 threaded through the tunneling straw, and then the tunneling straw removed from the tunnel while maintaining the stimulation leads 12 in place within the tunnel.

The stimulation leads 12 are then connected directly to the IPG 14 by inserting the proximal ends of the stimulation leads 12 within connector ports located on the connector 42 of the IPG 12 or connected to lead extensions 24, which are then inserted into the connector ports of the IPG 14. The IPG 14 can then be operated to generate electrical pulses that are delivered, through the electrodes, to the targeted tissue, and in particular, the dorsal column and dorsal root fibers within the spinal cord and lower back region of the patient in a manner described in further detail below. As there shown, the CP 18 communicates with the IPG 14 via the RC 16, thereby providing a means to control and reprogram the IPG 14.

With respect to SCS, the electrodes 26 may be arranged medio-laterally with respect to the spinal cord, or alternatively, the electrodes 26 may be arranged rostro-caudally with respect to the spinal cord.

Figure 5:
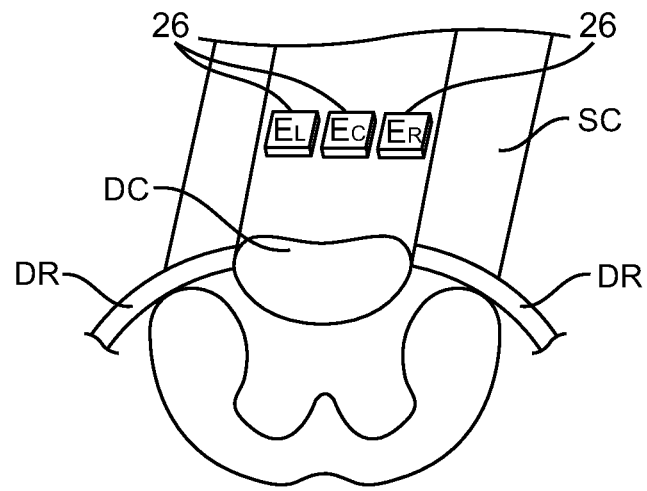
FIG. 5 is a perspective view of the electrodes of one stimulation lead of FIG. 2 medio-laterally located over the spinal cord of a patient.
Figure 6:
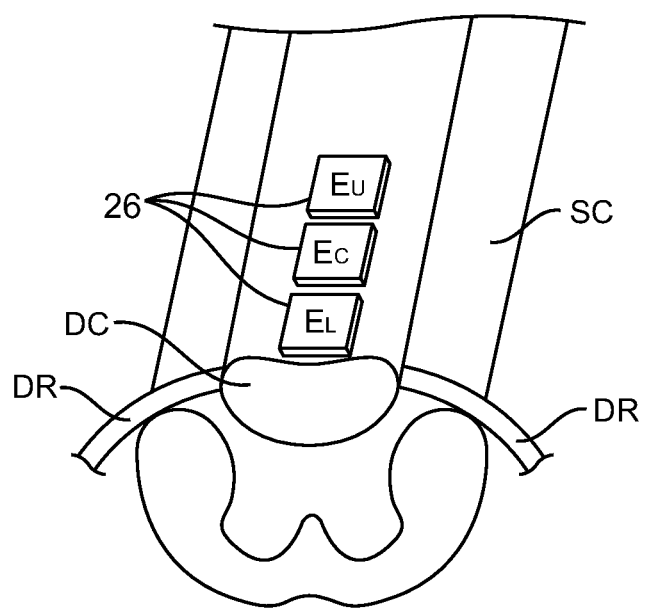
FIG. 6 is a perspective view of the electrodes of another stimulation lead of FIG. 2 rostro-caudally located over the spinal cord of a patient.

For example, as shown in FIG. 5, the surgical lead 12(1) illustrated in FIG. 3 can be used to arrange three electrodes 26 (one center electrode $E_C$ located over the center of the dorsal column DC nerve fibers, a left electrode $E_L$ laterally placed from the center of the DC nerve fibers adjacent the left dorsal root DR nerve fibers, and a right electrode $E_R$ laterally placed from the center of the dorsal column DC nerve fibers adjacent the right dorsal root DR nerve fibers) transverse to the axis of the spinal cord SC (medio-laterally). As another example, as shown in FIG. 6, the percutaneous lead 12(2) illustrated in FIG. 3 can be used to arrange three electrodes 26 (an upper (or rostral) electrode $E_U$, a center electrode $E_C$, and a lower (or caudal) electrode $E_L$) along the axis of the spinal cord SC (rostro-caudally) over the dorsal column DC nerve fibers. The system 10 has application in a wide variety of SCS regimens.

Figure 8:
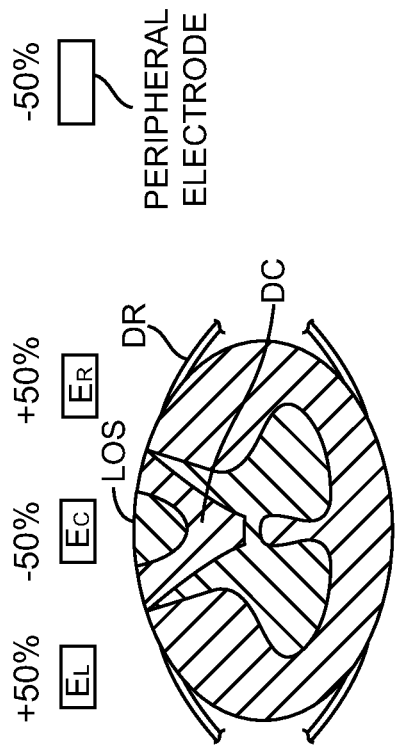
FIG. 8 is a cross-section diagram of a spinal cord, particularly illustrating a locus of stimulation induced by the medio-lateral electrode arrangement of FIG. 5.
Figure 7:
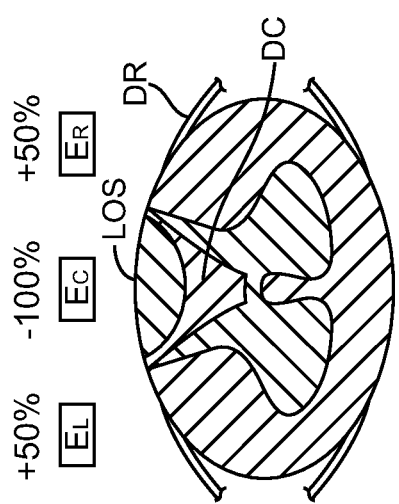
FIG. 7 is a cross-section diagram of a spinal cord, particularly illustrating a locus of stimulation induced by a prior art medio-lateral electrode arrangement.

For example, neurostimulation regimens that use the surgical paddle lead 12 to medio-laterally arrange the electrodes 26 in the manner illustrated in FIG. 5 can be used to shape of the AP generating neural region of the spinal cord in order to prevent the generation of APs in non-target neural fibers. As shown in FIGS. 7 and 8, the center electrode $E_C$ is placed over the dorsal column DC nerve fibers, while the left electrode $E_L$ and the right electrode $E_R$ are respectively placed over the dorsal root DR nerve fibers on both sides of the dorsal column DC nerve fibers.

A conventional SCS regimen that sinks all of the electrical current within the stimulation lead(s) implanted within the spinal column will serve as a reference for the stimulation regimens performed in accordance with the present inventions, and will thus be initially described with reference to FIG. 7. In this conventional stimulation regimen, the left and right electrodes $E_L$ and $E_R$ are activated as anodes and the center electrode $E_C$ is activated as a cathode. In the illustrated embodiment, the two electrodes $E_L$, $E_R$ are each sourcing 50% of the total current (e.g., 2 mA each), and the center electrode $E_C$ is sinking 100% of the total current (e.g., 4 mA). The combination of the hyperpolarizing electric fields generated by the left and right electrodes $E_L$, $E_R$ and the depolarizing electric field generated by the center electrode $E_C$ results in an area within the dorsal column DC that is at or above the depolarization threshold. This area, which has an overall depth and width, is the locus of stimulation LOS.

In the conventional stimulation regimen described above, it is desirable that the locus of stimulation LOS be as narrow as possible without increasing the depth of the LOS, thereby stimulating target nerve fibers within the dorsal column DC, while preventing stimulation of non-target nerve fibers within the dorsal roots DR. This would require an increase in the hyperpolarizing electrical field generated by the left and right electrodes $E_L$, $E_R$ over that illustrated in FIG. 7. That is, strengthening of the hyperpolarizing electric fields created by the electrodes $E_L$, $E_R$ tends to result in a narrowing of the locus of stimulation LOS, because it weakens the lateral edges of the depolarizing electric field created by the center electrode $E_C$. However, this necessarily may result in an increase in the current sunk by the center electrode $E_C$, thereby increasing the depth of the locus of stimulation LOS, which may lead to undesirable outcomes (e.g., discomfort or undesirable reflexive activity).

The system 10 may be used to solve this problem by effectively increasing the AP threshold of the dorsal root DR nerve fibers relative to the AP threshold of the dorsal column DC nerve fibers. As illustrated in FIG. 8, one example of a stimulation regimen in accordance with a present invention involves creating a locus of stimulation LOS that has a smaller width and the same depth. Here, in the same manner described above with respect to FIG. 7, the left and right electrodes $E_L$, $E_R$ are activated as anodes and the center electrode $E_C$ is activated as a cathode. However, the amount of current sourced at the left and right electrodes $E_L$, $E_R$ should be sufficient to create a hyperpolarizing electric field that is strong enough to narrow the locus of stimulation LOS to the smaller width. For example, the current sourced at the left and right electrodes $E_L$, $E_R$ may be increased (e.g., 4-8 mA each) in order to strengthen the hyperpolarizing electric fields.

Notably, sinking all of the current sourced by the left and right electrodes $E_L$, $E_R$ into the center electrode $E_C$ could result in a depolarizing electric field that would undesirably increase the depth of the locus of stimulation LOS. In this case, however, a portion of the current sourced by the left and right electrodes $E_L$, $E_R$ is sunk into at least one of the electrodes 26 of the stimulation leads 12(2) peripherally implanted in the lower back region of the patient. As a result, only a portion of the current sourced by the left and right electrodes $E_L$, $E_R$ is sunk into the center electrode $E_C$ (in this case, 50%), thereby allowing the intensity of the depolarizing electric field created by the center electrode $E_C$ to be reduced to a level that does not increase the depth of the locus of stimulation LOS compared to that illustrated in FIG. 7. Thus, the electrical current sunk at the center electrode $E_C$ provides therapy to the bodily region (i.e., the dermatome) corresponding to the stimulated portion of the spinal cord, and in this case, the upper leg regions, while the electrical current concurrently sunk at the peripheral electrode(s) provides therapy to the peripheral region, and in this case, the lower back region.

Alternatively, rather than narrowing the locus of stimulation LOS in both directions, the locus of stimulation LOS may be narrowed in only one direction. Here, only one of left and right electrodes $E_L$, $E_R$ is activated as an anode. In this case, 100% of the total current is being sourced at the left electrode $E_L$ or right electrode $E_R$, while the current is being sunk at the center electrode $E_C$ and peripheral electrodes.

Figure 9:
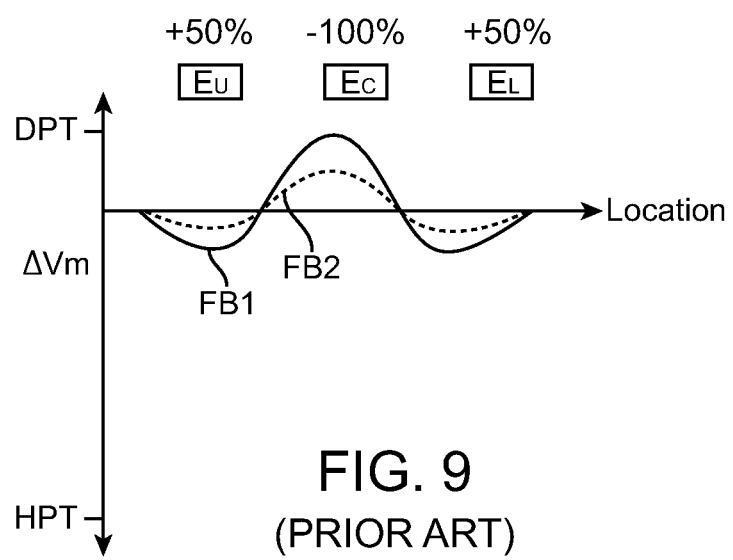
FIG. 9 is a graph of the changes in neural fiber transmembrane potential in first and second fibers bundles induced by a prior art rostro-caudal electrode arrangement.
Figure 10:
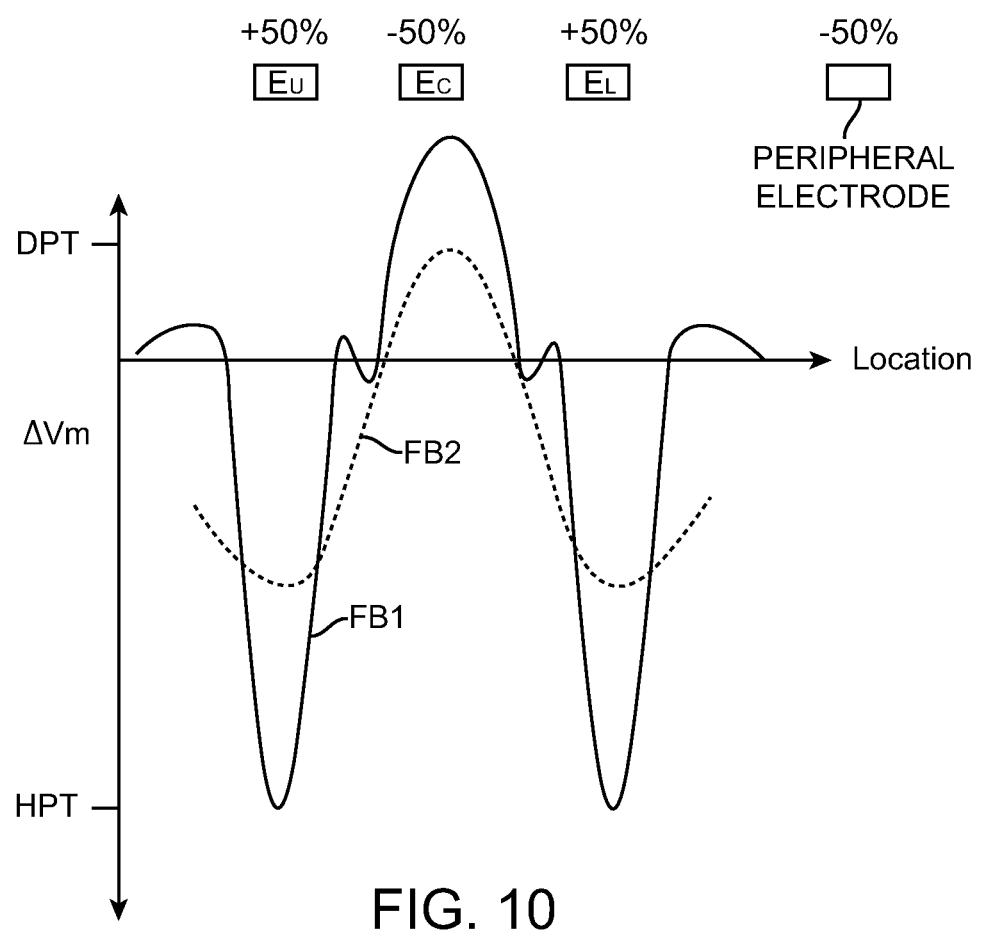
FIG. 10 is a graph of the changes in neural fiber transmembrane potential in first and second fibers bundles induced by the rostro-caudal electrode arrangement of FIG. 6.

As another example, neurostimulation regimens that use one percutaneous lead 12(2) to rostro-caudally arrange the electrodes 26 can be used to selectively block APs in neural fibers. As shown in FIGS. 9 and 10, the changes in transmembrane potential ($\Delta V_m$) of neural fibers in fiber bundles that are in the vicinity of the electrodes 26 are graphically illustrated when electric fields are generated by the electrodes 26 during the neurostimulation regimens. The neurostimulation regimens are discussed in the context of first and second fiber bundles FB1 and FB2. In the illustrated examples, the first fiber bundle FB1 is the closest fiber bundle to the electrodes 56, and the second fiber bundle FB2 is the next closest fiber bundle to the electrodes 56.

A conventional SCS regimen that sinks all of the electrical current within the stimulation lead implanted within the spinal column will serve as a reference for the stimulation regimens performed in accordance with the present inventions, and will thus be initially described with reference to FIG. 9. In this conventional stimulation regimen, the upper and lower electrodes $E_U$, $E_L$ are activated as anodes, and the center electrode $E_C$ is activated as a cathode. In the illustrated embodiment, 50% of the total current (e.g., 2 mA) is being sourced at each of the upper and lower electrodes $E_U$, $E_L$, and 100% of the total current (e.g., 2 mA) is being sunk at the center electrode $E_C$.

The depolarizing electric field generated by the center electrode $E_C$ is sufficient to create APs in some of the neural fibers in the first fiber bundle FB1. In other words, the depolarization threshold DPT has been met for the first fiber bundle FB1 in the tissue adjacent the center electrode $E_C$. The depolarizing electric field generated by the center electrode $E_C$ is substantially weaker at the second fiber bundle FB2 and is below the AP-creating depolarization threshold DPT. The locus of stimulation is, therefore, defined by the portion of the depolarizing electric field generated by the center electrode $E_C$ that is at or above the depolarization threshold DPT.

The upper and lower electrodes $E_U$, $E_L$, which are functioning as anodes in the stimulation regimen illustrated in FIG. 9, will create hyperpolarizing electric fields in the neural tissue adjacent the upper and lower electrodes $E_U$, $E_L$. When the electric field is at or above the hyperpolarization threshold HPT, the neural fibers within the electric field will block APs that were fired at other points along the fibers. It should be noted here that the magnitude of the hyperpolarization threshold HPT has been estimated to be about 2 to 8 times the magnitude of the depolarization threshold DPT. The hyperpolarizing electric fields generated by upper and lower electrodes $E_U$ and $E_L$ in the exemplary stimulation regimen are below the hyperpolarization threshold HPT at the first fiber bundle FB1. As such, APs in the fiber bundle FB1 that fired at points in the neural fibers adjacent to center electrode $E_C$ will not be blocked at points adjacent the upper and lower electrodes $E_U$, $E_L$. The hyperpolarizing electric fields generated by the upper and lower electrodes $E_U$, $E_L$ will, of course, be even weaker at the second fiber bundle FB2.

In the conventional stimulation regimen described above, the generation of APs in the fibers within the second fiber bundle FB2 will require an increase in the depolarizing electric field generated by the center electrode $E_C$ over that illustrated in FIG. 9. There may be instances where the generation of APs in the first fiber bundle FB1, which necessarily results from the creation of a depolarizing electric field that is strong enough to meet the depolarization threshold DPT at the second fiber bundle FB2, may lead to undesirable outcomes (e.g. discomfort or undesirable reflexive activity) for the patient.

The system 10 may be used to solve this problem by preventing APs generated in the first fiber bundle FB1 from reaching the brain or end organ. Specifically, as illustrated in FIG. 10, one example of a stimulation regimen in accordance with the present invention involves creating local AP blocks that prevent APs created within a portion of the depolarizing electric field that is at or above the depolarization threshold DPT from traveling in both directions beyond the stimulation site. The effective locus of stimulation is, therefore, the region of neural fibers that are generating APs that are not blocked at other portions of the stimulation site.

Here, in the same manner described above with respect to FIG. 9, the upper and lower electrodes $E_U$, $E_L$ are activated as anodes and the center electrode $E_C$ is activated as a cathode. However, the amount of current sunk at the center electrode $E_C$ is sufficient to create a depolarizing electric field that is strong enough to meet the depolarization threshold DPT at the second fiber bundle FB2 and cause fibers within the second fiber bundle to generate APs. Such a depolarizing electric field will, of course, also cause the fibers in the first fiber bundle FB1 to generate APs.

However, at least a substantial portion of the APs in the first fiber bundle FB1 will be prevented from passing electrode $E_U$ by the hyperpolarization. In particular, at least a substantial portion of the APs (i.e., >10-20%) are blocked by hyperpolarizing tissue in the first fiber bundle FB1, located on opposite sides of the tissue in the first fiber bundle FB1 that is generating the APs, to at least the hyperpolarization threshold HPT. This may be accomplished by significantly increasing the level of current sourced from the upper and lower electrodes $E_U$, $E_L$, as compared to the level illustrated in FIG. 9 (e.g., about 2.5 mA each), in order to reach the hyperpolarization threshold HPT within the first fiber bundle FB1 at the upper and lower electrodes $E_U$, $E_L$.

Notably, sinking all of the current sourced by the upper and lower electrodes $E_U$ and $E_L$ at the center electrode $E_C$ could result in a depolarizing electric field that would meet or exceed the depolarization threshold DPT in fiber bundles well beyond the second fiber bundle FB2. In this case, however, a portion of the current sourced by the upper and lower electrodes $E_U$ and $E_L$ is sunk into at least one of the electrodes of the stimulation leads 12(2) peripherally implanted in the lower back region of the patient. As a result, only a portion of the current sourced by the upper and lower electrodes $E_U$, $E_L$ is sunk into the center electrode $E_C$ (in this case, 50%), thereby allowing the intensity of the depolarizing electric field created by the center electrode $E_C$ to be reduced to a level where the depolarization threshold DPT will not be met in fibers beyond the second fiber bundle FB2. Thus, the electrical current sunk at the center electrode $E_C$ provides therapy to the bodily region (i.e., the dermatome) corresponding to the stimulated portion of the spinal cord (in this case, the buttocks), while the electrical current concurrently sunk at the peripheral electrode(s) provides therapy to the peripheral region, and in this case, the lower back region.

Alternatively, rather the blocking AP in both directions, the stimulation regimen may involve locally blocking APs in a single direction generated in the first fiber bundle FB1. Here, only one of upper and lower electrodes $E_U$, $E_L$ is activated as an anode. In this case, 100% of the total current is being sourced at the upper electrode $E_U$ or lower electrode $E_L$, while the current is being sunk at the center electrode $E_C$ and peripheral electrodes.

Notably, it is often desirable to cycle the PNFS function on and off (i.e., cycling the sinking of the cathodic electrical current at the peripheral electrodes on and off) while continually performing the SCS function (i.e., continually sinking the cathodic electrical current at the spinal electrodes). For example, with reference to FIG. 11, the IPG 14 may be programmed to alternatively burst the cathodic electrical pulses at the peripheral electrodes on and off, as shown by the cathodic current (peripheral) waveform, while maintaining the cathodic electrical pulses at the SCS electrodes on, as shown by the cathodic current (SCS) waveform. The IPG 14 is programmed to continually burst the anodic electrical pulses at the SCS electrodes on, as shown by the anodic current (SCS) waveform.

Figure 11:
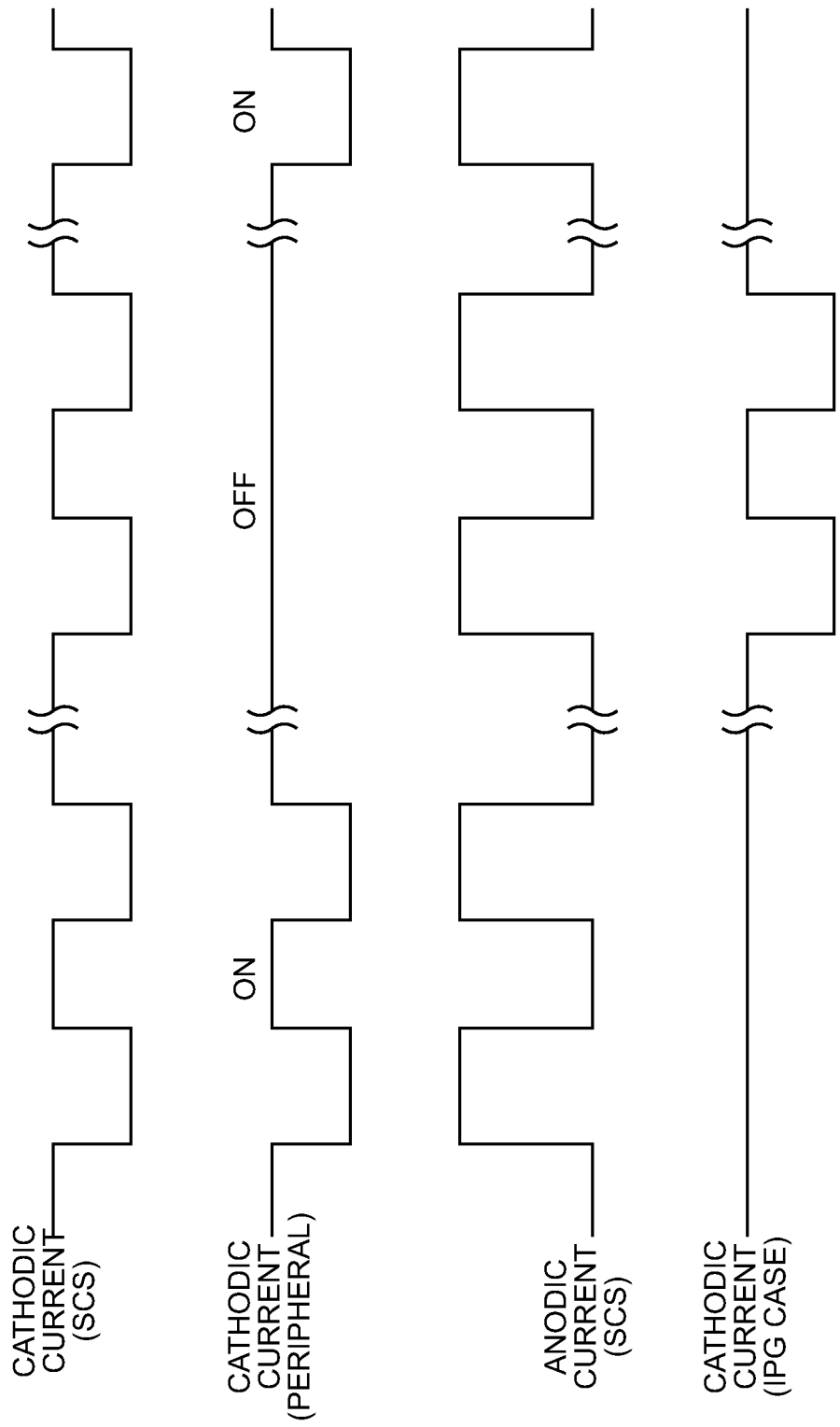
FIG. 11 is a graph of pulse timing diagrams used to sink and source electrical current pulses in accordance with one technique of the present inventions.

As can be appreciated from FIG. 11, the magnitude of the anodic electrical pulses is equal to the sum of the magnitude of the cathodic electrical pulses at the SCS electrodes and the magnitude of the cathodic electrical pulses at the peripheral electrodes (when on), and it is desirable to maintain the magnitude of the anodic electrical current during the entirety of the SCS function. In this case, the cathodic current that would have been used for the PNFS function had it not been cycled off must be redirected to another electrode. That is, the cathodic current in excess of that needed for the SCS function must be sunk to another electrode, so that the magnitude of the anodic electrical current can be maintained. Thus, as shown in FIG. 11, the IPG 14 may be programmed to burst cathodic electrical pulses at the IPG case 40 during the burst-off duration of the cathodic electrical pulses at the peripheral electrodes. Preferably, the magnitude of the cathodic electrical pulses bursted on at the IPG case 40 is the same as the magnitude of the cathodic electrical pulses bursted on at the peripheral electrodes, so that the SCS function is not adversely affected. While this may not completely eliminate undesirable pocket stimulation, it will reduce undesirable stimulation of the spinal cord.

It may also be desirable to cycle the PNFS function between different peripheral electrodes (i.e., cycling the sinking of the cathodic electrical current between different sets of peripheral electrodes) to provide therapy to different lower back regions, while continually performing the SCS function (i.e., continually sinking the cathodic electrical current at the spinal electrodes). For example, with reference to FIG. 12, the IPG 14 may be programmed to alternatively burst the cathodic electrical pulses on between first and second sets of peripheral electrodes, as shown by the first and second cathodic current (peripheral) waveforms, while maintaining the cathodic electrical pulses at the SCS electrodes on, as shown by the cathodic current (SCS) waveform. The first set of peripheral electrodes may be carried by one stimulation lead 12(2) shown in FIG. 4, and the second set of peripheral electrodes may be carried by the other stimulation lead 12(2) shown in FIG. 4. For the purposes of this specification, a set of peripheral electrodes may comprise one or more electrodes. The IPG 14 is programmed to continually burst the anodic electrical pulses at the SCS electrodes on, as shown by the anodic current (SCS) waveform.

As can be appreciated from FIG. 12, the magnitude of the anodic electrical pulses is equal to the sum of the magnitude of the cathodic electrical pulses at the SCS electrodes and the magnitude of the cathodic electrical pulses at the peripheral electrode set that is currently on. The magnitudes of the cathodic electrical pulses at the peripheral electrode sets are the same, so that the magnitude of the anodic electrical current during the entirety of the SCS function can be maintained. No cathodic electrical pulses need be bursted on at the IPG case 40, since any cathodic current in excess of that needed for the SCS function is distributed between the first and second peripheral electrode sets.

It should be noted that cathodic electrical pulses at the SCS electrodes and peripheral electrodes may be concurrent, meaning that the respective pulses begin and end at the same times. However, it may be desirable for the durations of the cathodic electrical pulses to differ from each other, which must be compensated for.

For example, as shown in FIG. 13, the pulse width of the cathodic current at the SCS electrodes may be longer than the pulse width of the cathodic current at the peripheral electrodes, such that the pulse width of cathodic current at the SCS electrodes has a portion that is temporarily coincident with the pulse width of the cathodic current at the peripheral electrodes, and a portion that is not temporarily coincident with the pulse width of the cathodic current at the peripheral electrodes. Although the temporarily non-coincident portion is shown at the end of the pulse, it should be noted that it can alternatively occur at the beginning of the pulse.

As can be appreciated from FIG. 13, the magnitude of the anodic electrical pulses is equal to the sum of the magnitude of the cathodic electrical pulses at the SCS electrodes and the magnitude of the cathodic electrical pulses at the peripheral electrodes (during the temporarily coincident portion), and it is desirable to maintain the magnitude of the anodic electrical current during the entirety of the SCS function. In this case, the cathodic current that would have been used for the PNFS function during the temporarily non-coincident portion (i.e., the extended portion of the SCS pulse after the PNFS pulse is over) must be redirected to another electrode. That is, the cathodic current in excess of that needed for the SCS function during the temporarily non-coincident portion must be sunk to another electrode, so that the magnitude of the anodic electrical current can be maintained.

Thus, as shown in FIG. 13, the IPG 14 may be programmed to generate cathodic electrical pulses at the IPG case 40 (or alternatively another peripheral electrode or electrodes or both the IPG case and peripheral electrode(s)) during the temporarily non-coincident portion of the cathodic pulse. Preferably, the magnitude of the cathodic electrical pulses generated at the IPG case 40 is the same as the magnitude of the cathodic electrical pulses generated at the peripheral electrodes, so that the SCS function is not adversely affected.

As another example, as shown in FIG. 14, the pulse width of the cathodic current at the SCS electrodes may be shorter than the pulse width of the cathodic current at the peripheral electrodes, such that the pulse width of cathodic current at the peripheral electrodes has a portion that is temporarily coincident with the pulse width of the cathodic current at the SCS electrodes, and a portion that is not temporarily coincident with the pulse width of the cathodic current at the SCS electrodes. Although the temporarily non-coincident portion is shown at the end of the pulse, it should be noted that it can alternatively occur at the beginning of the pulse. To extend the width of the PNFS pulse after the SCS pulse is over, the IPG 14 may be programmed to generate anodic electrical pulses at the IPG case 40 (or alternatively, another peripheral or SCS electrode or electrodes, or both the IPG case and peripheral and/or SCS electrode(s)) during the temporarily non-coincident portion of the anodic pulse, as shown in FIG. 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient, comprising:
   sinking first electrical current into at least a first one of a plurality of electrodes adjacent spinal cord tissue of the patient, thereby providing therapy to a first region of the patient;
   sinking second electrical current into at least one electrode adjacent peripheral tissue of the patient remote from the spinal cord tissue, thereby providing therapy to a second region of the patient, wherein the first and second electrical currents are concurrently sunk; and
   sourcing at least a portion of the first electrical current and at least a portion of the second electrical current from at least a second one of the plurality of electrodes.

2. The method of claim 1, further comprising:
implanting the plurality of electrodes adjacent the spinal cord tissue; and
implanting the at least one electrode adjacent the peripheral tissue.

3. The method of claim 1, wherein the peripheral tissue is located in the lower back of the patient.

4. The method of claim 1, wherein the first region of the patient is a leg region and the second region of the patient is a lower back region.

5. The method of claim 1, wherein all of the first electrical current and all of the second electrical current is sourced from the at least second one of the plurality of electrodes.

6. The method of claim 1, wherein each of the first and second electrical currents comprises a plurality of electrical pulses.

7. The method of claim 6, wherein the electrical pulses of the first and second electrical currents are concurrent.

8. The method of claim 6, wherein the first electrical current has a first pulse width, and the second electrical current has a second pulse width different from the first pulse width.

9. The method of claim 8, wherein the first pulse width is longer than the second pulse width, such that the first pulse width has a first portion that is temporally coincident with the second pulse width, and a second portion that is not temporarily coincident with the second pulse width, wherein the at least portion of the second electrical current is sunk into the at least one electrode during the first portion of the first pulse width, and the at least portion of the second electrical current is sunk into either or both of a case of an implantable pulse generator and at least one other electrode adjacent the peripheral tissue during the second portion of the first pulse width.

10. The method of claim 8, wherein the first pulse width is shorter than the second pulse width, such that the second pulse width has a first portion that is temporally coincident with the first pulse width, and a second portion that is not temporarily coincident with the first pulse width, wherein the at least portion of the second electrical current is sourced into the at least second electrode during the first portion of the second pulse width, and is sourced into any combination of a case of an implantable pulse generator, at least one other electrode adjacent the peripheral tissue, and at least a third of the plurality of electrodes during the second portion of the second pulse width.

11. The method of claim 1, further comprising cycling the sinking of the second electrical current on and off at the at least one electrode while continually sinking the first electrical current.

12. The method of claim 11, wherein the at least a portion of the second electrical current is sunk into a case of an implantable pulse generator when the second electrical current at the at least one electrode is cycled off.

13. The method of claim 11, further comprising sinking the second electrical current into at least another electrode adjacent the peripheral tissue, thereby providing therapy to a third region of the patient, wherein the sinking of the second electrical current into the at least other electrode is cycled on when the sinking of the second electrical current into the at least one electrode is cycled off.

14. The method of claim 1, wherein the plurality of electrodes is arranged medio-laterally along the spinal cord tissue.

15. The method of claim 14, wherein the at least first electrode is adjacent dorsal column neural fibers of the spinal cord tissue, the at least second electrode is adjacent dorsal root neural fibers of the spinal cord tissue, the sunk first electrical current generates action potentials in the dorsal column neural fibers, and the sourced at least a portion of the first electrical current increases the action potential threshold of the dorsal root neural fibers.

16. The method of claim 1, wherein the electrodes are arranged rostro-caudally along the spinal cord tissue.

17. The method of claim 16, wherein the at least first electrode is a first distance from a first neural fiber bundle and is a second greater distance from a second neural fiber bundle, the sunk first electrical current generates action potentials in the first and second neural fibers bundles, and the sourced at least a portion of the electrical current blocks at least some of the action potentials in the first neural fiber bundle.

18. The method of claim 1, wherein the first and second electrical currents are generated by a single implantable pulse generator.

19. The method of claim 18, wherein the plurality of electrodes are carried by a first lead, and the at least one electrode is carried by a second lead, the method further comprising coupling the first lead and the second lead to the implantable pulse generator.

20. The method of claim 19, wherein the first lead and the second lead are coupled to the implantable pulse generator via a lead splitter.

* * * * *